United States Patent [19]

Dykes et al.

[11] Patent Number: 5,303,591
[45] Date of Patent: Apr. 19, 1994

[54] ULTRASONIC INSPECTION SYSTEM WITH IMPROVED PULSER AND RECEIVER CIRCUITS

[75] Inventors: Edward R. Dykes; William F. Splichal, Jr., both of San Jose, Calif.

[73] Assignee: General Electric Company, San Jose, Calif.

[21] Appl. No.: 694,730

[22] Filed: May 2, 1991

[51] Int. Cl.$^5$ .............................................. G01N 29/04
[52] U.S. Cl. ........................................ 73/620; 73/623; 73/629
[58] Field of Search .................. 73/620, 622, 623, 629, 73/632, 633

[56] References Cited

U.S. PATENT DOCUMENTS

3,982,425 9/1976 McLain ................................. 73/632
4,052,887 10/1977 Sheridan et al. ..................... 73/622
4,114,457 9/1978 Thun ..................................... 73/632

Primary Examiner—John E. Chapman
Attorney, Agent, or Firm—J. S. Beulick

[57] ABSTRACT

The remote inspection of seam welds in reactor vessels is improved through the utilization of a pulser network which is inductively isolated from the transducer circuit to which it applies an excitation signal. Through the utilization of a step-up transformer, the pulser network may perform in conjunction with linear d.c. power supplies of lower voltage rating. The inductive coupling between circuits also serves to provide for the positive communication off of switching devices such as SCRs employed for excitation signal triggering. To avoid ground path induced noise, a different ground path is employed for the pulser network as for the transducer circuit. The transducer circuit ground path is that associated with a manipulator and, for example, a reactor vessel itself. Thus, the transducers employed may come in contact with the surface of the vessel being inspected. In similar fashion, an inductive coupling is provided between the transducer circuit and a pre-amplfying receiver circuit. This same inductive coupling may be employed to enhance the impedance match between the FET-based amplification stage and the impedance defining components of the transducer circuit.

9 Claims, 5 Drawing Sheets

ULTRASONIC INSPECTION SYSTEM WITH IMPROVED PULSER AND RECEIVER CIRCUITS

BACKGROUND OF THE INVENTION

Reactor vessels employed in the nuclear power industry, as well as similar vessels used with large industrial facilities in general are fabricated as welded plate structures. Typically, reactor vessels will be formed with longitudinal and circumferential seam welds, as well as nozzle welds and the like at their cylindrical or main body portions and with corresponding welds at their top and bottom heads. Because of the criticality of maintaining the structural integrity of power reactor vessels over their somewhat extended lifespans, regulatory agencies such as the Nuclear Regulatory Commission (NRC) require extensive examination of the welds within predetermined intervals. Typically, non-destructive examination and evaluation of the welded structures are carried out during scheduled shut-downs planned for such activities as refueling and the like.

Because such planned shut-downs involve a power production outage, the efficiency of their execution is most important to industry. However, the weld inspection procedure is complex, requiring control over man-rem exposure, and thus calling for remotely controlled examination systems which themselves must be capable of operating within the environment of gamma radiation. Where boiling water reactors (BWR) are the subject of inspection, advantages have been recognized for an internal approach wherein the water media within the reactor vessel or additionally that within the refueling cavity serve to isolate personnel from radiation originating from the nuclear fuel. Remotely controlled manipulators generally are employed to physically move and position inspection heads or search units carrying ultrasonic inspection transducers and the like to positions adjacent the various vessel weldments. Ultrasonic test (UT) examination then is carried out under the control of remote stations which may be located as far is several hundred feet from the manipulator carried search units. In locating weld flaws, piezoelectric crystal based transducers are excited, preferably at their resonant frequencies by a remotely generated pulse delivered from along long lengths of shielded cable. The same or another such transducer retained crystal then reacts to a received echo of much lower signal level to form an evaluating signal which is returned along a lengthy communications cable for data acquisition at the remote control station. To achieve adequate excitation of the transducers, resort generally is made to relatively higher level, d.c. power supplies, for example switching supplies in the 300 Vdc to 1,000 Vdc range. These power supplies, in and of themselves, are sources of undesirable noise and much of the excitation energy generated by them will be dissipated by the shielded transmission cabling employed for its delivery. Cable terminations must be precisely installed to avoid interfering signals arising due to energy reflections up and down the length of the cables. Signal loss conditions are further experienced with respect to the low signal level responses transmitted for data acquisition for the same reasons in addition to the attenuation of the cable acting upon very low level signals. Important information can be lost as ultrasonic signals are attenuated to below the electronic noise level of the system.

Noise phenomena present within the reactor facility also have been seen to impact upon the quality of the low level signals arising due to targets in the specimen under inspection. Nuclear power reactor installations and other industrial facilities generally are constructed having a plant grounding system including a buried electrical base mat or grid to which various plant components are electrically coupled. The reactor pressure vessel will be coupled along one path to ground as will plant machinery. Similarly, electrical control instrumentation will be grounded through a segregated linkage. Notwithstanding the presence of these grounding systems, components such as the reactor pressure vessel typically exhibit ground potentials varying several volts, for example, from instrumentation grounds. As a consequence, an opportunity for ground potential based noise generation is present. This has called for elaborate structuring and positioning procedures for the transducer-carrying search units to avoid development of any electrical communication between the transducer and its associated electronics with the reactor vessel wall and structuring connected thereto.

From the foregoing, it may be observed that improvements in the techniques for transducer operation, both in noise avoidance and in excitation and echo response approaches will be well received by many industries. In addition, any such improvements in the nuclear industry must be evolved with instrumentation or circuitry which is reliable under the harsh operating environment posed by gamma radiation if the previously discussed limitations on currently available instruments are to be overcome. Any loss of reliability will be manifested by costly time losses occurring with shut-down maintenance activities and attendant lengthening of the interval of outage.

SUMMARY

The present invention is addressed to inspection apparatus and associated circuitry for carrying out ultrasonic examinations. Particularly suited for application to the nuclear power industry (wherein remotely controlled manipulators position UT transducers in adjacency with reactor pressure vessel walls), the pulser, transducer, and receiver circuits of the apparatus are associated with unique isolation features to segregate the grounding paths in order to achieve electrical noise avoidance. Communication or operative interaction between these circuits is by transformers. Such transformer coupling prevents ground currents from circulating between the reactor component under inspection and the signal receiving networks.

The pulser circuit of the apparatus employs a solid-state switch in the form of a silicon controlled rectifier (SCR) which performs in conjunction with an energy storing capacitor and the primary winding of an isolating transformer coupling the pulser function to the transducer to generate a signal for effecting its excitation. A back EMF developed through this inductance is advantageously employed for commutating the SCR to an assured off-stage following capacitor discharge generating the excitation signal. By configuring the inter-circuit coupling transformers in step-up fashion, addi7 tional advantage is realized. For example, more desirable, lower voltage level linear d.c. power supplies may be used with the pulser circuit. Further, an apparent impedance matching may be developed between the input or transducer circuit and the amplification stage of the receiver circuit. All of these advantageous characteristics are achieved with a significantly low number of circuit components. The low component count contributes not only to improved circuit reliability, but enhances circuit resistance to the deleterious effects of gamma radiation within which the circuits are called upon to perform.

Another feature of the invention provides inspection apparatus of a variety employing a transducer mounted with a manipulator to carry out the examination of a metal component within a facility having a first grounding path, and further having second grounding paths for instrumentation. A transducer circuit is provided which is coupled with the transducer and is connected during the examination with the first grounding path. The circuit has an input network for receiving an excitation drive signal to excite the transducer and an output network for providing a response signal. A pulser network is connected during the examination with a second grounding path and is responsive to a trigger signal for generating an excitation signal. A first coupling arrangement is provided having a first winding coupled with the pulser network and a second winding coupled within the transducer circuit input network and is responsive to the pulser network generated excitation signal for effecting the inductive conveyance thereof to the second winding to provide a corresponding excitation drive signal. A receiver circuit is provided which is responsive to the transducer circuit output network response signal for effecting the conveyance of a corresponding response output signal to a data acquisition facility.

Other objects of the invention will, in part, be obvious and will, in part, appear hereinafter.

The invention, accordingly, comprises the apparatus and system possessing the construction, combination of elements, and arrangement of parts which are exemplified in the following detailed disclosure.

For a fuller understanding of the nature and objects of the invention, reference should be had to the following detailed description taken in connection with the accompanying drawings.

DETAILED DESCRIPTION OF THE INVENTION

Figure 1:
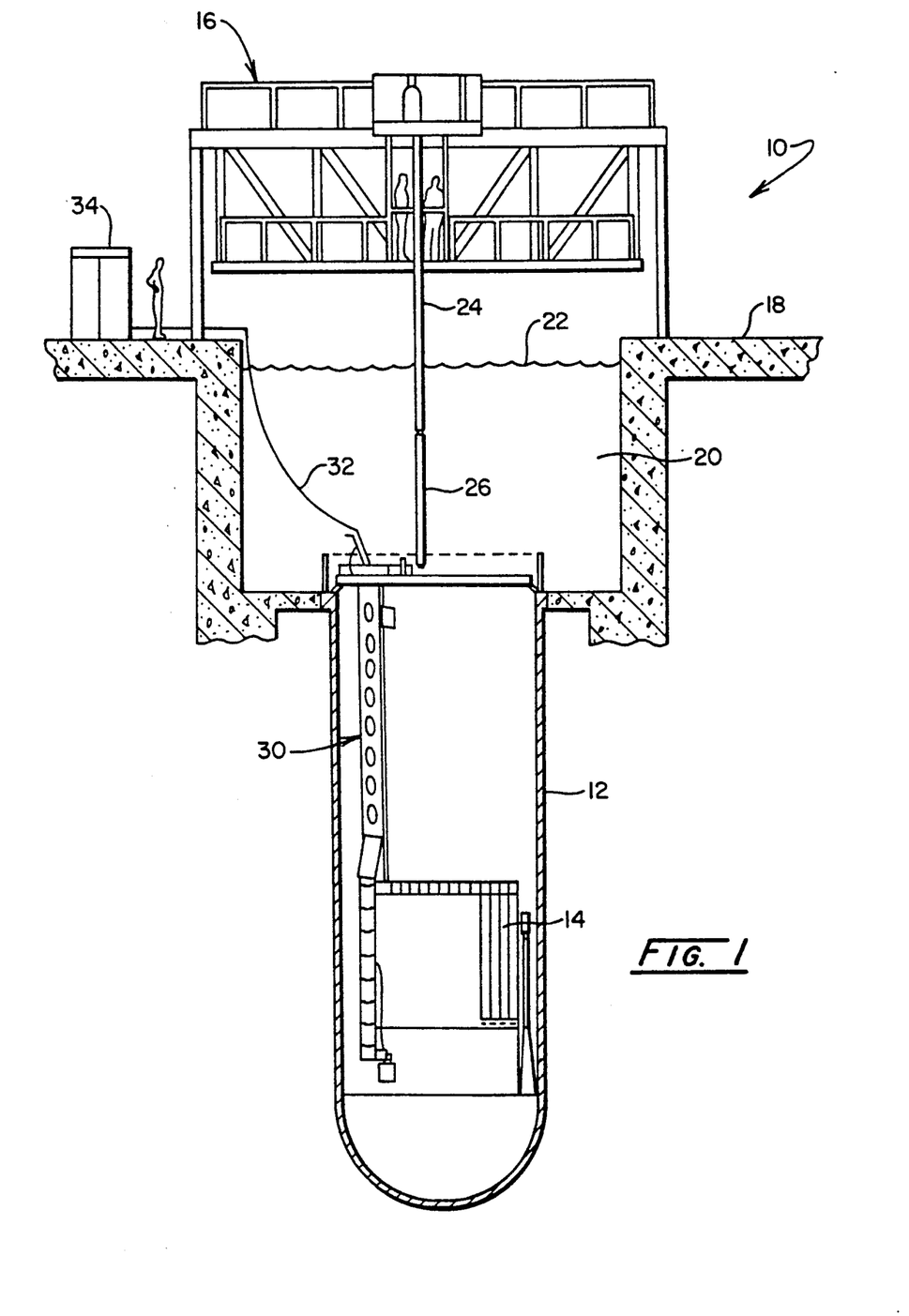
FIG. 1 is a perspective view of a nuclear facility showing refueling and weld seam inspection activities during a planned shut-down.

An important utilization of the apparatus and system of the invention is in conjunction with nuclear power facilities. During planned or scheduled shut-downs of these facilities wherein collateral activities such as refueling and the like are undertaken, weld seam inspection may be carried out. Preferably, this inspection is performed internally such that the water contained within the reactor vessel forms a shield serving to minimize radiation exposure to personnel. Looking to FIG. 1, an example of a boiling water reactor (BWR) component of a nuclear power facility is represented schematically at 10. The facility 10 is seen to include a reactor pressure vessel 12, the core of which at 14 is shown undergoing a refueling procedure during a planned shut-down. In this regard, the top head or cap of the vessel 12 is removed and refueling access to the core is provided from a refueling bridge 16. Refueling bridge 16 is seen mounted at the refueling floor 18 of the facility 10 and extends over an upper, water-filled pool or refueling cavity 20. The water level within the cavity 20 is shown at 22. For the purposes of the inspection to be described, this cavity 20 may or may not be filled with water. The refueling activity is represented by a refueling manipulator 24 shown in the process of maneuvering a fuel assembly 26. Simultaneously with this refueling procedure, a weld seam inspection manipulator assembly, represented generally at 30, is seen to be in operation and under the control of control stations and the like. These control and data acquisition stations are located remotely from the vessel 12, for example at the refueling floor 18. In this regard, a flexible control and communications cable 32 is seen extending from the manipulator 30 to sub-station cabinetry 34 at the refueling floor 18.

Figure 2:
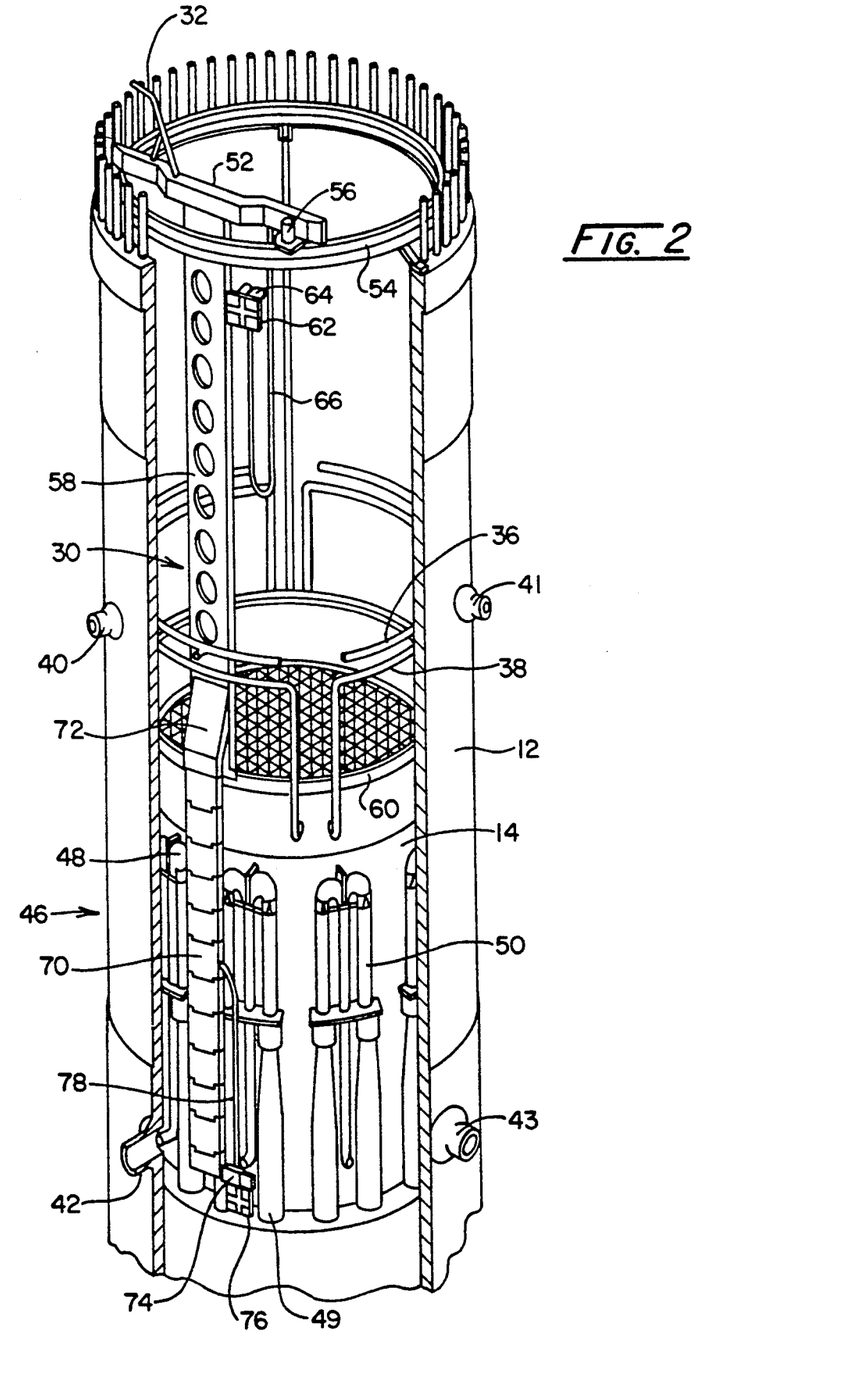
FIG. 2 is a partial sectional view of a reactor vessel and inspection manipulator mechanism with portions broken away to reveal internal structure.

Looking to FIG. 2, the reactor vessel 12 is represented at a higher level of detail, particularly showing the structuring of manipulator assembly 30. In the figure, the core again is represented at 14 and situated above the core are components typically encountered within such vessels 12, such as spargers 36 and 38, as well as a variety of nozzles as at 40–43. The core 14 is located at the belt-line region 46 of the vessel 12 and, also located at this general region, within a downcomer annulus are a sequence of elongated vertically oriented jet pumps as at 48–50. As is apparent, any manipulator such as at 30 must be configured to maneuver about these various components within the vessel 12.

Manipulator 30 is configured having an upwardly disposed circumferential car 52 which partially spans and is driveably rotated about an upper guide ring 54, for example, by a position controlling motor 56. Supported from the circumferential car 52 is a vertically oriented mast 58 which extends to and is additionally movably supported upon a lower guide ring 60. Guide rings 54 and 60 are installed by inspection personnel in the course of preparing the vessel 12 for seam weld examination procedures. Vertically movable along the elongate edge of mast 58 is an upper search unit or head 62 carrying several of piezoelectric based ultrasonic testing transducers (not shown). The search unit 62 is manipulated by a vertical travel mechanism 64 and is in control and communication connection through a shielded cable 66 with circuitry developed in accordance with the instant invention within a protected enclosure (not shown) which may be mounted upon the mast 58 or circumferential car 52. From that circuitry, communication is further made via cabling as at 32 with the remote control and data acquisition facilities located, for example, on the refueling floor 18. Manipulator 30 further is capable of maneuvering an inspection assembly within the beltline region 46 of vessel 12 through the utilization of a linked belt 70 which is coupled to the lower portion of mast 58 through a swivel guide 72. Attached to one edge of the linked belt 70 is a horizontal travel mechanism 74 which, in turn, supports a lower search unit or head 76 which is structured in the same manner as search unit 62. The horizontal travel mechanism is capable of moving vertically along one edge of the linked belt 70 and is further capable of maneuvering the search unit 76 horizontally. Through the utilization, for example, of water jets, the linked belt assembly can be held against the vessel wall. Communication between the search unit 76 and circuitry employed with the instant invention is by shielded cable, such as a coaxial cable 78.

Figure 3:
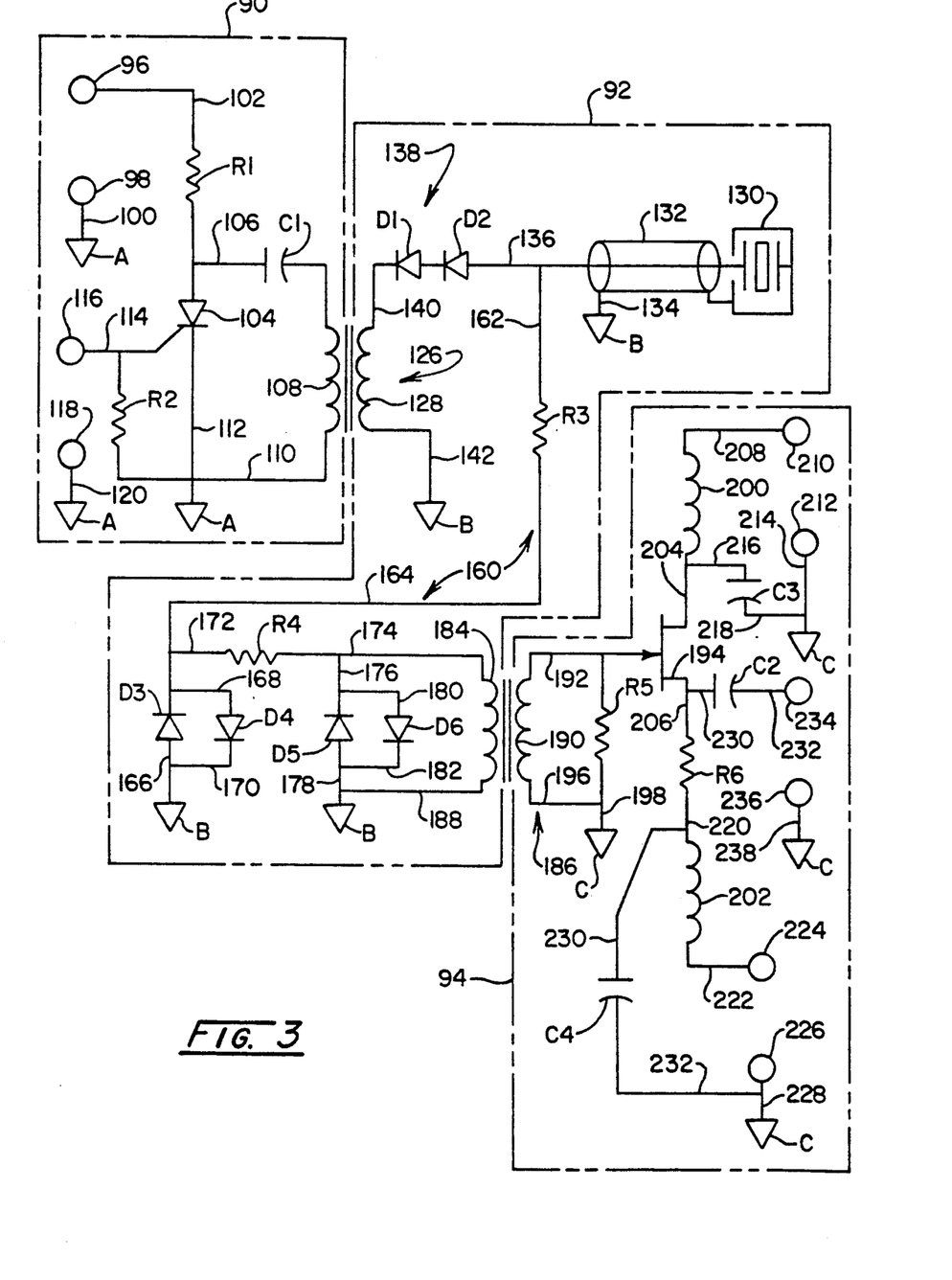
FIG. 3 is an electronic schematic diagram showing the pulser and pre-amplifier functions of the invention.

Referring to FIG. 3, a pulser and pre-amplifier circuit developed for the purpose of operating each of the piezoelectric transducers within search units 62 and 76 is revealed. These pulsers and pre-amplification circuits are located, as noted, in one of the linked belt 70 components or in the region of the mast 58. The circuit is generally configured having a pulser network or circuit represented at the boundary line 90; a transducer circuit represented within the boundary line 92; and a receiver circuit represented within the boundary line 94.

Pulser network 90 functions to develop an excitation signal which is conveyed to transducer circuit 92. Rather than perform in conjunction with the relatively high level switching power supplies commonly encountered for such devices, network 90 performs in conjunction with a d.c. linear power supply which may be, for example, within about the 40 to 100 Vdc range. Such power supplies are readily available and exhibit lower electrical noise. The input to network 90 from this power supply is represented at terminals 96 and 98. Note that terminal 98 is seen coupled via line 100 to a ground designated A. Ground path A is a specific pulser circuit ground coupled with the instrumentation, for example, at the refueling floor 18 which also is associated with the noted linear power supply. This d.c. power input of relatively lower level is applied via line 102 through a current limiting resistor R1 to the anode of a gated thyristor present as a silicon controlled rectifier (SCR) 104 and via line 106 in series to capacitor C1 and a primary winding 108 and thence via lines 110 and 112 to the noted ground path A. Line 112 additionally is seen to be connected with the cathode of SCR 104. The gate of SCR 104 at line 114 is seen directed to one terminal 116 of a control input which includes terminal 118 coupled, in turn, via line 120 to ground path A. A resistor R2 within line 114 extending to gate line 110 provides some load for the relatively low voltage level input trigger signal and also serves to prevent inadvertent gating on of the SCR 104 by shunting any spurious voltages (dv/dt) to ground.

During the operation of network 90, capacitor C1 is charged through resistor R1 in accordance with a predetermined time constant established by their parameter values. The charge level may reach, for example, a value of 100 volts. Upon the application of a trigger signal to terminals 116 and 118, SCR 104 is gated into conduction and capacitor C1 discharges through the primary winding 108 of the pulser transformer 126 to ground A with a large negative pulse. Inductor winding 108 is the primary winding of a step-up transformer, the physically isolated secondary winding of which is shown within transducer circuit 92 at 128. A typical turns ratio between winding 108 and winding 128 is 1:4 although the turns ratio may be any desired value suitable for the particular application. Thus, the negative going pulse asserted at primary winding 108 is inductively coupled and magnified into secondary winding 128. Accordingly, the more practical linear d.c. power supply becomes available for the requirement of transducer excitation.

The transducer or input circuit as at 92 is operatively associated with a corresponding transducer of the search units. One such transducer is represented within the circuit 92 at 130. Communication between the transducer 130 and circuit 92 is by a shielded cable such as the schematically depicted coaxial cable 132. The shielding of cable 132 is connected to another distinct ground as depicted by line 134 and ground B. This ground tap is to an "input circuit and transducer" ground which is segregated from ground path A and may be the same ground path associated with reactor vessel 12. Thus, this transducer ground may be at the potential of reactor pressure vessel 12 and the manipulator 30 without adversely affecting the operation of the circuit. The output transducer 130, as represented at line 136 extends to the input network 138 of circuit 92 which incorporates blocking diodes D1 and D2, connected in parallel and oppositely oriented, as represented at line 140 to secondary winding 128 and thence as represented at line 142 to the isolated transducer ground B. With the arrangement shown, as the primary winding 108 is excited from the discharge of capacitor C1, a corresponding negative going pulse is witnessed at line 136 which is employed to provide a half cycle form of excitation to transducer 130. Blocking diodes D1 and D2 permit conduction during the initial negative excursion of the pulse witnessed at winding 128 but block any interaction with the pulser network 90 thereafter. Generally, it is preferred that the transducer 130 be excited with a half sinewave or half cycle pulse to achieve its excitation at the center value of its resonant frequency. This permits its most efficient excitation. In general, the length of the submerged coaxial cable 132 will not exceed about two meters, the variable distance from the submerged circuit of FIG. 3 and search units at 62 or 74.

Figure 4:
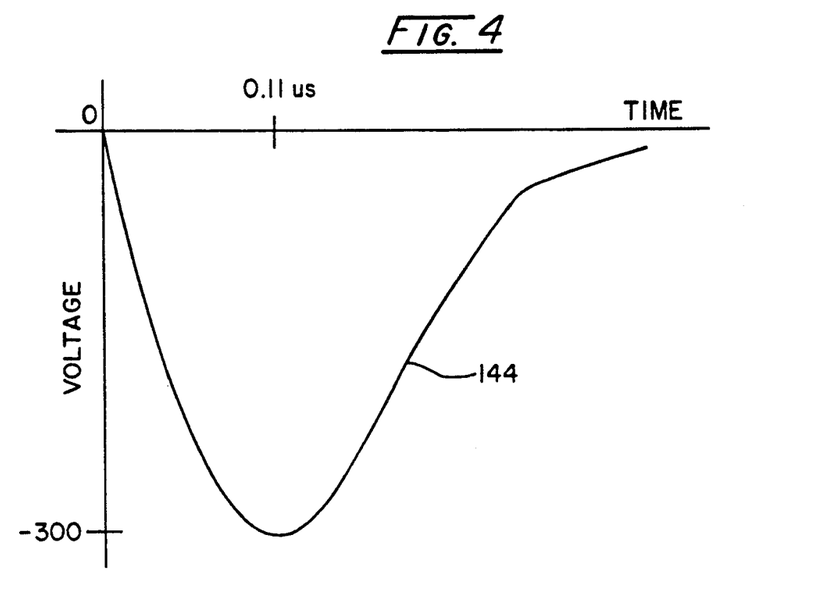
FIG. 4 is a representative pulser circuit waveform developed in conjunction with the circuit of FIG. 3.

Looking momentarily to FIG. 4, a typical pulse shape generated at the network 138 is represented at 144. Waveform 144 is that employed, for example for driving a 2.25 MHz transducer. The pulse shape 144, in general, is determined by the size of capacitor C1. In practice, the circuitry is tuned to the characteristics of the transducer as at 130 by adjusting the size of capacitor C1. The voltage on the circuit at the input terminals is adjusted to set the pulse height. Typically, capacitor C1 will be selected in a range of about 1,000 picofarads to 20,000 picofarads.

Figure 5:
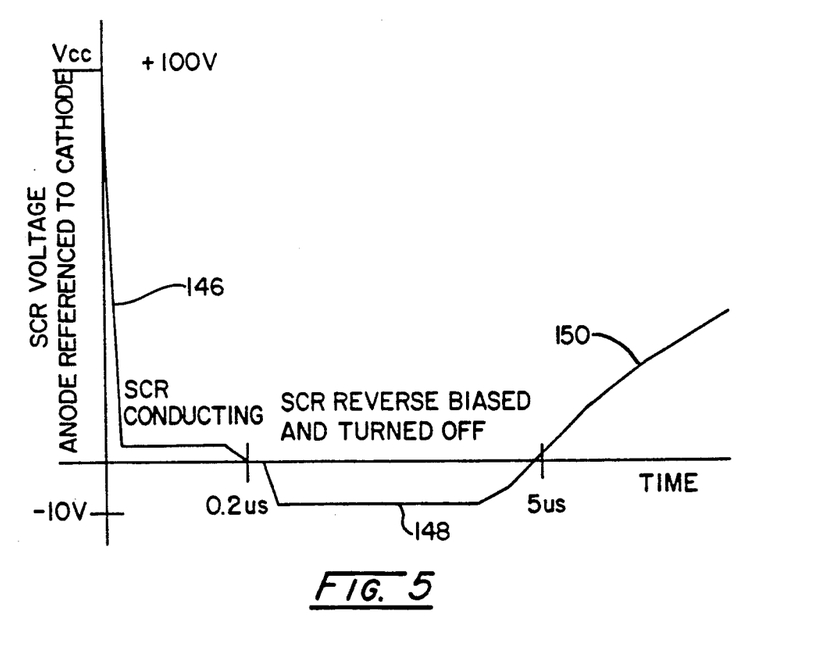
FIG. 5 is a typical voltage waveform at the anode of an SCR employed with the pulser circuit of the invention showing a commutation feature.

Returning to pulser network 90, in conventional transducer drive systems, where SCRs are employed for switching purposes, they are turned off by the procedure of current starvation. Of particular advantage with the utilization of inductive coupling between network 90 and circuit 92, a reverse EMF inductive surge will be witnessed following the discharge of capacitor C1 through primary winding 108. Blocking diodes D1 and D2 promote this development of reverse EMF. That reverse EMF will occur across SCR 104 for an interval of time and thus positively turn it off or commutate it. Looking momentarily to FIG. 5, a typical waveform showing this activity is represented at 146, 148, and 150 in association with the earlier-noted exemplary power supply of 100 volts d.c. Waveform component 146 represents the conducting phase of SCR 104 in response to a gating or trigger signal input. At about 0.2 microseconds, there is seen to occur a current starvation whereupon, as represented at waveform component 148 extending substantially between 0.2 microseconds and 5 microseconds, the SCR 104 is reverse biased or commutated off. This commutation length, is of a relatively significant interval assuring the off-state condition. Following that interval, a recovery phase represented at waveform component 150 ensues wherein capacitor C1 is recharged substantially to supply voltage and the SCR 104 remains off in keeping with its conventional operational characteristics.

The pulse repetition rate as developed by pulser network 90 is derived with respect to the time constant evolved between resistor R1 and capacitor C1. Generally, by adjusting the size or resistance value of resistor R1 an optimum desired performance may be evolved. Typically, a pulse repetition rate of 100 to 5,000 pulses per second is selected. With the arrangement shown, a variety of advantages accrue with the circuit. Through the use of a step-up transformer 126 the demands for the power supply diminish to the extent that readily available low voltage linear power supply with low noise characteristics may be used. The transformer coupling between the primary winding 108 and secondary winding 128 developed between network 90 and circuit 92 functions to, in turn, isolate the ground path A from ground path B. This reduces electrical noise in the circuit and, permits the conductive components of the transducers at 130 to touch the vessel wall or any other structure to be inspected with no adverse affect on the circuitry. Further, as noted above, through the reverse EMF characteristic developed with the transformer 126, SCR 104 is positively commutated off following each triggering.

Now looking to the receiving function of the transducer circuit 92, as represented at the output network components thereof represented at 160, following the occurrence of the excitation pulse generated from network 90, a quiescent interval ensues wherein the transducer 130 is poised to respond to a small echoing or return pulse. Transducer 130, when used in a pulse-echo mode, will respond to this received or reflected pulse and generate a response signal. Alternatively, where a "pitch-catch" transducer arrangement is utilized, a separate transducer will be employed for the reception of the reflected or return pulse. Blocking diodes D1 and D2 function to isolate the output network 160 during this reception interval. As the faint return signal is received, it is transmitted from the transducer 130 to line 136. Typically, the signal will be in the 200 or 300 millivolt range or lower. This signal then is directed via line 162 and resistor R3 to line 164. Resistor R3 functions to provide a damping resistance to the excitation pulses asserted upon circuit 92, as well as to provide an impedance match with respect to the coaxial cable 132. Line 164 is seen directed to diode D3, the cathode of which is coupled via line 166 to ground path B. Also associated with diode D3 in reversed fashion is diode D4 which is seen coupled to line 164 through line 168 and to line 166 through line 170. Also coupled to line 164 is line 172, resistor R4 and line 174. Coupled to line 174 is line 176 which, in turn, is directed to the cathode of diode D5, the anode of which at line 178 is coupled to the earlier-noted ground path B. A reverse oriented diode D6 also is coupled via line 180 to line 176 and via line 182 to line 178. Back-to-back diodes D3, D4 and D5, D6 function to shunt the large excitation pulse initiated from pulsing network 90 to ground path B. Resistor R4 positioned between these diode pairs provides a second level of isolation protecting the receiver circuit 94. However, during the reception of the weak response signal, any diversion of such signal is blocked by the diode pairs D3, D4 and D5, D6, and the return signal is directed via line 174 to the primary winding 184 of a step-up transformer 186. The opposite side of winding 184 is directed via line 188 to ground path B. The secondary winding 190 of transformer 186 responds to the applied response signal, which now will be stepped up to a higher voltage value. For example, the turns ratio between primary winding 184 and secondary winding 190 may be 1:4. This stepped-up voltage signal is applied via line 192 to the gate terminal of a field effect transistor (FET) 194 which serves as an amplification stage of the receiver circuit 94. The opposite side of secondary winding 190 is coupled via lines 196 and 198 to another, segregated "receiver" ground path, C. This path will extend, for example, to the instrumentation power supply associated with circuit 94. Line 198 is seen coupled to line 192 and incorporates a resistor R5 which will be selected having relatively higher value, for example in the range of about 100 Kilohms. Resistor R5 functions to establish bandwidth, as well as participates in an impedance matching function. It may be observed that through the employment of magnetic isolation provided by transformer 186, the ground path C is isolated from ground path B as well as from ground path A. This serves to substantially abate noise and improve the signal generating capability of the entire inspection system. Of particular importance in the utilization of transformer 186 is the noise resistance characteristic of FET device 194. These devices are, in themselves, relatively quiet with respect to noise generation. However, the step-up performance of transformer 186 functions to provide an equivalent match of the noise resistance characteristics of the FET 194 with the impedance exhibited by transducer circuit 92, for example, as exhibited by the primary circuit of transformer 186 including resistors R3 and R4. That impedance essentially is magnified to a correspondence or equivalence with the noise resistance characteristic of device 194. Receiver circuit 94 is somewhat conventional in its construction, FET 194 performs in conjunction with a current amplification and filtering function including inductive windings or chokes 200 and 202 within respective lines 204 and 206. The opposite side of winding 200 extends via line 208 to a power supply input terminal 210. The corresponding grounding terminal 212 is coupled via line 214 to ground path C and a filter capacitor C3 coupled intermediate lines 216 and 218 also is directed to ground path C. Correspondingly, the opposite electrode of FET 194 is coupled via line 206, resistor R6 and line 220 to one side of winding 202, the opposite side of which at line 222 extends to a power supply terminal 224 of opposite polarity to that at 210. The ground terminal corresponding to terminal 224 is shown at 226 coupled via line 228 to ground path C. Additionally, a filter capacitor C4 is seen coupled to intermediate lines 230 and 232 extending, in turn, to respective lines 220 and 228. In general, a power input of one polarity, for example, +8 Vdc, is applied across terminals 210 and 212, whereas a negative input power supply, for example −8 Vdc, is applied with respect to terminals 224 and 226.

The resultant amplified signal is provided at lines 230 and 232 through coupling capacitor C2 to terminal 234, while the corresponding output ground is provided at terminal 236 which, in turn, is coupled to ground path C via line 238.

Figures 6A, 6B:
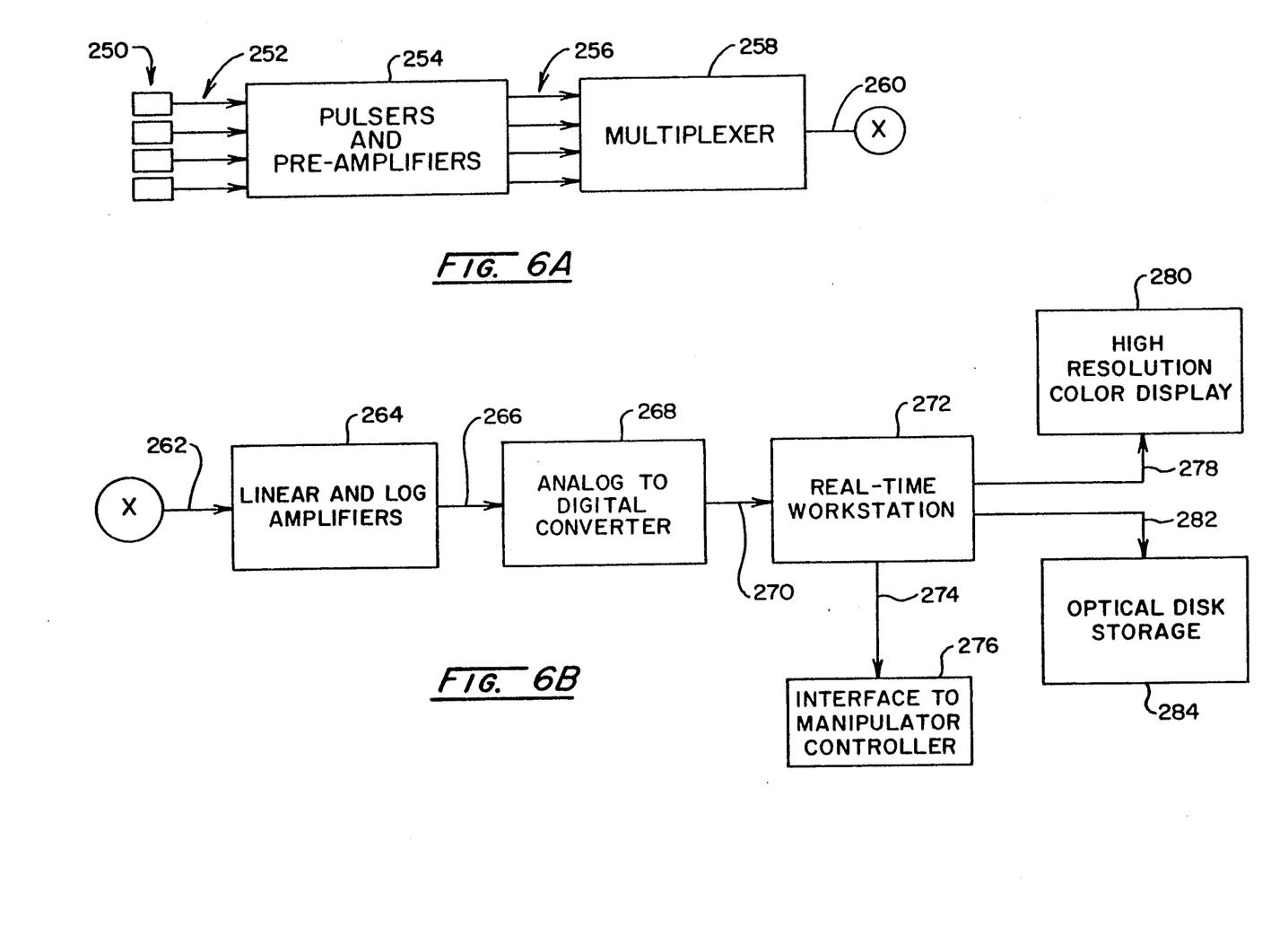
FIGS. 6A and 6B combine to show a schematic block diagram of an example of a system within which the pulser and pre-amplifier components of the invention perform.

Looking to FIG. 6A, a block diagrammatic representation of the components of the apparatus at hand which are maintained under water in reasonably close adjacency with the search units 62 and 76 is revealed. In general, the length of communication between the circuits and the circuitry thus far described will be about 2 meters. In the figure, an array of transducers is represented at 250 having cable inputs represented by corresponding line array 252 to pulser and preamplifier functions represented at block 254. This function, as represented at block 254, corresponds with the circuit of FIG. 3, one such circuit being provided for each transducer. The resultant response output signals as well as triggering inputs for transducer selection are promulgated at lead array 256 from a multiplexing function represented at block 258. This multiplexing function then conveys the resultant signals to a data acquisition and control facility as represented by line 260 leading to node X. Typically, as many as 16 transducer circuits can be controlled by one multiplexer. Several multiplexers may be used to achieve a configuration with as many transducers as may be desired.

Looking to FIG. 6B, the control data acquisition facilities are generally described in block schematic fashion. Node X is seen to reappear in conjunction with line 262 leading to an amplification function represented at block 264. Block 264 provides a linear and logarithmic amplification function, whereupon resultant data signals are directed as represented by line 266 to an analog-to-digital conversion function represented at block 268. Following conversion, the resultant digital data then are directed, as represented by line 270 and block 272 to a real-time workstation for operator evaluation and appropriate treatment. The workstation represented at block 272 also is interfaced to the controller for manipulator 30 as represented by line 274 and block 276. Data also are displayed at a high resolution color display as represented by line 278 and block 280. Additionally, the substantial volume of data evolved during the examination procedures at hand are stored, through the utilization of optical disk media as represented by line 282 and block 284.

An examination of the circuit represented at FIG. 3 reveals that it fully performs with substantially few electronic components. In general, the failure rate for any circuit subjected to the rigorous environment involved elevates as the components required to perform requisite functions increase in number. This holds particularly true in environments subjected to gamma radiation as encountered in the application described above. Of course, certain, for example, transformers 126 and 186, are inherently radiation resistant. The active components such as SCR 104 can be pre-evaluated for radiation resistance. In this regard, a type GA301A SCR has been employed with success. Other SCR devices particularly identified as being of a nuclear radiation resistant variety will be in the GA100, 101, 102 and 200 series. The circuit of FIG. 3 has been found to operate without significant degradation of performance at radiation levels above 5,000 rads per hour. A smaller number of components, of course, improves reliability of the circuit as well as does its employment of relatively lower input power supplies, for example, to the pulser network 90. Further, electronic noise is minimized, for example, by matching the noise resistance characteristic of the FET 194 based amplifier stage to the low impedance of the transducer output network 160 through the employment of the step-up characteristic of transformer 186. Of course, through the mutual magnetic isolation of circuits 90, 92, and 94, no extraneous noise is introduced via the ground paths.

Since certain changes may be made in the above described system and apparatus without departing from the scope of the invention herein involved, it is intended that all matter contained in the description thereof or shown in the accompanying drawings shall be interpreted as illustrative and not in a limiting sense.

We claim:

1. Inspection apparatus of a variety employing a transducer mounted with a manipulator to carry out the examination of a metal component within a facility having a first grounding path, and further having second grounding paths for instrumentation, comprising:
   a transducer circuit coupled with said transducer connected during said examination with said first grounding path, having an input network for receiving an excitation drive signal to excite said transducer and an output network for providing a response signal;
   a pulser network connected during said examination with a said second grounding path, and responsive to a trigger signal for generating an excitation signal;
   first coupling means having a first winding coupled within said pulser network and a second winding coupled within said transducer circuit input network and responsive to said pulser network generated excitation signal for effecting the inductive conveyance thereof to said second winding to provide a corresponding said excitation drive signal; and
   a receiver circuit responsive to said transducer circuit output network response signal for effecting the conveyance of a corresponding response output signal to a data acquisition facility.

2. The inspection apparatus of claim 1 including:
   second coupling means having a third winding coupled within said transducer output network and a fourth winding coupled within said receiver circuit, and responsive to said output network response signal for effecting the inductive conveyance thereof to said fourth winding to provide said response output signal; and
   wherein said receiver circuit is connected during said examination with a said second grounding path.

3. The inspection apparatus of claim 1 including:
   second coupling means having a third winding coupled within said transducer output network and a fourth winding coupled within said receiver circuit, and responsive to said output network response signal for effecting the inductive conveyance thereof to said fourth winding to provide said response output signal; and
   wherein said receiver circuit is connectable with a said second grounding path separate from the said second grounding path to which said pulser network is connectable.

4. The inspection apparatus of claim 1 in which said pulser network and said transducer circuit are mounted upon said manipulator.

5. The inspection apparatus of claim 1 in which said first coupling means is a step-up transformer configured for isolating said pulser network from said first ground path, said first winding being a primary winding providing a first step-up turns ratio with respect to said second winding predetermined for deriving said excitation drive signal.

6. The inspection apparatus of claim 5 including a linear d.c. power supply connected in power supply relationship with said pulser network.

7. The inspection apparatus of claim 6 in which said power supply provides a power output in a range of about 40 to 100 Vdc.

8. The inspection apparatus of claim 2 in which:
said receiver circuit includes an amplifier stage exhibiting a given noise resistance;
said transducer output network exhibits a predetermined value of impedance;
said second coupling means is a step-up transformer configured for isolating said receiver network from said first grounding path, said third winding being a primary winding and said fourth winding being a secondary winding providing a second step-up turns ratio with respect to said third winding which is selected for deriving said response output signal.

9. The inspection apparatus of claim 8 in which said second predetermined turns ratio is selected for effecting an equivalent impedance match between said transducer output network predetermined value of impedance and said amplifier stage noise resistance.

* * * * *